(12) United States Patent
    Adamovics

(10) Patent No.: US 9,357,925 B2
(45) Date of Patent: Jun. 7, 2016

(54) METHOD AND APPARATUS FOR SCANNING 3D DOSIMETERS

(71) Applicant: John Adamovics, Skillman, NJ (US)

(72) Inventor: John Adamovics, Skillman, NJ (US)

(*) Notice: Subject to any disclaimer, the term of this patent is extended or adjusted under 35 U.S.C. 154(b) by 46 days.

(21) Appl. No.: 14/447,666

(22) Filed: Jul. 31, 2014

(65) Prior Publication Data

US 2015/0036141 A1    Feb. 5, 2015

Related U.S. Application Data

(60) Provisional application No. 61/861,495, filed on Aug. 2, 2013.

(51) Int. Cl.

| *G01T 1/02* | (2006.01) |
| *G01T 1/00* | (2006.01) |
| *A61B 5/00* | (2006.01) |
| *G01T 7/00* | (2006.01) |
| *A61N 5/10* | (2006.01) |

(52) U.S. Cl.
CPC ............ *A61B 5/0073* (2013.01); *A61N 5/1071* (2013.01); *A61N 5/103* (2013.01); *G01T 1/02* (2013.01); *G01T 7/00* (2013.01)

(58) Field of Classification Search
CPC ...... A61B 5/0073; A61N 5/1071; G01T 1/02; G01T 7/00
USPC .................................................. 356/432–444
See application file for complete search history.

(56) References Cited

U.S. PATENT DOCUMENTS

| 3,440,420 | A  | * | 4/1969  | Attix ........................ G01T 1/06 |
|           |    |   |         | 250/472.1 |
| 3,783,292 | A  | * | 1/1974  | Alter ........................ G01T 1/02 |
|           |    |   |         | 250/475.2 |
| 5,319,210 | A  | * | 6/1994  | Moscovitch ............ G01T 1/026 |
|           |    |   |         | 250/472.1 |
| 5,369,717 | A  | * | 11/1994 | Attridge ......................... 385/12 |
| 6,594,336 | B2 | * | 7/2003  | Nishizawa et al. ............. 378/65 |
| 7,098,463 | B2 | * | 8/2006  | Adamovics ................. 250/474.1 |
| 7,633,048 | B2 | * | 12/2009 | Doran et al. ................... 250/221 |
| 7,738,945 | B2 | * | 6/2010  | Fauver et al. ................. 600/425 |
| 8,399,858 | B2 | * | 3/2013  | Yoder ........................ G01T 1/10 |
|           |    |   |         | 250/473.1 |
| 2010/0103512 | A1 | * | 4/2010 | Ranoux et al. ................. 359/398 |
| 2010/0193695 | A1 | * | 8/2010 | Yeow ....................... G01T 1/026 |
|              |    |   |        | 250/370.07 |
| 2012/0170049 | A1 | * | 7/2012 | Doran ........................... 356/496 |
| 2013/0078411 | A1 | * | 3/2013 | Gaska et al. ..................... 428/68 |

OTHER PUBLICATIONS

Bosi et al, "Light-scattering-induced artifacts in a complex polymer gel dosimetry phantom", Applied Optics May 1, 2009, vol. 48, No. 13, pp. 2427-2434.*
Phantom Patient for Stereotactic End-to-End Verification (STEEV) 2012 advertisement: http://www.meddevicedepot.com/PDFs/038Brochure.pdf.*

* cited by examiner

*Primary Examiner* — Tri T Ton
*Assistant Examiner* — Jarreas C Underwood

(57) ABSTRACT

The present invention discloses a device to measure optical properties of a three-dimensional transparent dosimeter, and a method to use the device to produce a valid, reproducible, and quantitative image of optical properties across essentially the entire volume of the transparent dosimeter. The invention provides significant and useful improvements over existing practice.

3 Claims, 6 Drawing Sheets

METHOD AND APPARATUS FOR SCANNING 3D DOSIMETERS

BACKGROUND OF THE INVENTION

Field of the Invention

The invention relates to an improved optical scanning apparatus and method of use for the measurement of the three-dimensional distribution of optical properties within the volume of a transparent object. The invention is directed to the field of Optical Computed Tomography (OCT) Dosimetry. The invention is particularly useful for, but not limited to, treatment planning, verification, and control in the field of medical radiotherapy. The invention advances the field of OCT Dosimetry by providing an efficient scanning system, coupled with modified solid refractive index media, which eliminates the undesirable liquid refractive index matching media currently utilized in OCT dosimetry, and delivers three-dimensional images with reduced edge artifacts.

Several Optical CT scanning systems have been disclosed. In particular, the problem of scanning radiation exposed dosimeters in order to evaluate medical radiotherapy plans has been addressed. For recent discussion see US Patent Application 2012/0179949 to Doran and Rankine et al *Medical Physics* 2013, 40 051701-1-051701-8. Currently, commercially available Optical CT scanners, and most of those disclosed in the scientific and patent literature, designed for medical radiotherapy treatment planning, all incorporate refractive index (RI) matching liquid media which imparts numerous undesirable aspects to these devices. Attempts to provide Optical CT scanners without RI matching media have been thus far inadequate and are not in current use. Optical CT has been utilized to produce computer-rendered images of various structures, which permit the transmission of incident light. Optical CT allows the generation of three-dimensional images through tomographic reconstruction of a stepped series of two-dimensional data arrays.

The key aim of optical data acquisition is to capture a set of line integrals, representing the absorption of light rays as they pass through the dosimeter. There is a significant complication, in the form of light refraction at the boundaries between media with different refractive indices. In current practice, this refraction problem is mitigated by immersion of the three dimensional dosimeter within a glass tank of liquid whose RI is matched as closely as possible to that of the dosimeter. Although the index matching method has led to acceptable results, there are a number of significant problems with the technique. Transparent liquids with refractive indices solvents in the appropriate range tend to be viscous, and require regular cleaning as dust and particles are accumulated within the liquid during use. Although RI matching with fluids is generally considered highly effective, there are several disadvantages associated with this approach.

It can be very time-consuming to obtain the required correspondence between the refractive indices of the fluid and dosimeter. This is normally achieved by mixing two liquids whose refractive indices bracket the desired RI of the dosimeter in order to fabricate a matching solution with the appropriate RI. Since the RI of the dosimeter is difficult to measure and therefore is rarely accurately determined, a process of empirical trial and error is employed, in which mixing the two liquids in different proportions until a suitable match between the RI of the dosimeter and that of the liquid is achieved. This process may take several hours for the large volumes of fluid (>5 L) which are used in the measurement of radiotherapy test objects.

The use of RI matching liquids is expensive and presents safety and disposal issues. Consequently, there is a pressing need to provide an RI matching enclosure which can be fabricated with an RI essentially identical with that of the dosimeter, but is not accompanied by the problems detailed herein.

A key part of the scanning procedure currently practiced is rotation of the irradiated dosimeter through a series of angular increments in order to store a multiplicity of two dimensional data arrays. Ideally, this rotation and measurement would be rapid, to minimize the time spent and expense of evaluating the three-dimensional radiation field captured within the dosimeter. However, when using an RI-matching liquid, this rotation rate is limited, because fluid drag causes vortices and other motions of the liquid and these may lead to significant artifacts in the reconstructed optical CT images. Optimizing matching RI by preparing a homogeneous mixture of organic liquids, filling the tank with same, loading the samples, drying the samples after use, and keeping the work area clean are all tasks that reduce significantly the throughput of the optical CT scanner. A particular concern is the need to avoid drops of matching liquid coming into contact with the outside of the two essentially parallel faces of the matching tank and thus obscuring the optical path.

As the RI of solids and liquids are temperature-dependent, a potential problem arises in cases in which the RI of the matching liquid has been optimized at a first temperature and the liquid and dosimeter are employed for tomographic evaluation at a second temperature. This may occur if the liquid and dosimeter are stored at different temperatures. In a non-limiting example, a dosimeter may be stored at low temperature after irradiation to preserve the stability of the data contained within. The temperature of the dosimeter and that of the matching liquid must be allowed to equilibrate to take full advantage of the function of the matching liquid. The time required for such an equilibration is costly. In addition, ambient temperature during dosimeter evaluation may differ from that during liquid RI optimization, which leads to sub-optimal scanning performance Because the RI of liquid is temperature dependent, and because liquids are susceptible to thermal convection currents, RI matching liquids are liable to form schlieren, or optical inhomogeneites, during OCT scanning. These "swirls" of altered RI, disrupt the projection images. The RI-matching liquid may therefore introduce additional optical scatter, which degrades the quality of the images. In addition, dust and other airborne contamination frequently settles within the matching liquid, providing additional optical scatter.

Organic liquids that are used as RI matching media have the potential to erode the surface of a dosimeter and leach the soluble dosimeter components into the liquid matching medium. The RI liquids have the potential to be toxic, have odors, and dissolve the silicone sealants of the glass tanks containing the matching liquids and the rubber "O"-rings used in the stepper motors. These caustic characteristics present a disadvantage in utilizing organic liquids as matching media.

The current invention, by eliminating the use of matching liquid, presents a convenient and efficient solution through the use of a solid RI matching block fabricated with a cavity with dimensions, volume, and RI essentially identical to those of the dosimeter. The use of solid RI matching media effectively eliminates the problems described above. In particular, the present invention provides, among others essential attributes designed to advance the art of optical scanning of three dimensional objects.

Because the matching block is fabricated from a solid transparent polymeric matrix essentially identical to that of the dosimeter, and may be molded, drilled, or otherwise fabricated to contain a cavity corresponding to the dosimeter, the RI of the dosimeter and matching block are essentially identical.

Use of the solid block of the invention represents an improvement in cost and efficiency of optical scanning of three dimensional objects in that the components used in manufacture are inexpensive and readily available in bulk; a block, once fabricated, may be reused a multiplicity of times; no experimentation or empirical blending of liquids to achieve an acceptable RI is required; dosimeters to be evaluated are quickly loaded and retrieved; no costly hazardous waste disposal is required.

Use of the solid block of the invention represents an improvement in the quality of images reconstructed by OCT. No vortices or shlieren develop during the evaluation process, the contamination of the matching media by environmental particles is obviated; the RI of the solid matching media is invariant with temperature change; the optical faces of the matching block are easily protected from obscuring contamination. In addition, edge artifacts are minimized so that essentially the entire volume of the three dimensional object is evaluated.

Use of the solid block of the invention represents a significant improvement in the impact of the scanning process upon the practitioner and the environment. Unlike the organic liquids currently in use as RI matching media, the solid block is not volatile; the solid block is non-toxic; the solid block is odor-free; the solid block is not caustic or harmful to other components of the scanning apparatus; and, unlike the need to treat RI liquid as hazardous waste, disposal of the solid block can be achieved by simple recycling.

Currently, optical scanning systems are in use. However, each suffers from disadvantages An optical CT scanner system has been described which uses a laser light source, which is used to scan a cylindrical dosimeter (Gore et al. 1996, *Physics in Medicine and Biology* 41, 2695-2704; U.S. Pat. No. 6,218,673 to Gore et al). The dosimeter is fabricated from aqueous gels containing chemical substances which, change properties upon exposure to radiation. This water soluble gel based dosimeter supported must be contained within a transparent container. Upon radiation the gel components polymerize to an insoluble opaque acrylate polymer in the dosimeter container. After irradiation the dosimeter is immersed in RI matching liquid and evaluation by OCT is achieved by comparison of optical contrast generated by light scattering of the irradiated opaque regions and those regions within the dosimeter which had not been irradiated. The plastic walls of the containers have an RI that differs from the gel and from the matching solvent. Consequently the additional refractive surfaces cause optical artifacts and limit the useable dosimeter volume to about 57% of the total dosimeter volume when a gel dosimeter in a cylinder shaped container with a radius of 6.6 cm and height of 10 cm is utilized. The optical scanner employs a laser light source, which is made to scan through a cylindrical dosimeter. The incident laser beam is reflected through 90 degrees by a first mirror and passed through the dosimeter contained within the RI matching medium. The transmitted beam is reflected through 90 degrees by a second mirror into a detector. A two-dimensional slice is produced by moving the first and second mirrors simultaneously along a carriage in a plane parallel to the optical axis. The dosimeter is rotated through a small angle in a plane orthogonal to the optical axis and another scan is measured. This scan and rotate process is repeated until the dosimeter has been rotated through 180 degrees. The entire volume of the dosimeter can only be scanned by employing a series of stepped rotations and axial translation of the dosimeter. Thus, after a large number of scans and stepped rotations of the dosimeter (180 scans when the step angle is set to 1 degree), the dosimeter must be indexed axially (e.g. so that the next scanned plane is 1 mm higher than the previous plane), and the scan-and-rotate process repeated. When the scanning is complete, a three-dimensional image is reconstructed after the data is subjected to filtration and back-projection (FBP) algorithms. While this scanner has successfully evaluated several dosimeters, it suffers from a number of drawbacks, which limit its usefulness. Transmission data requires correction to account for deviation of the laser beam from a normal incidence angle. The angle of incidence of the laser beam upon the surface of the tank was adjusted to 5 degrees from the window normal to reduce multiple reflections. The stepper-driven lateral mirror translation apparatus is vulnerable to error (precision motion of a relatively large structure is needed), resulting in a potential loss of resolution. The axial translation of the dosimeter required to measure slices perpendicular to the dosimeter axis represents another source of error. It is necessary to carefully align the center of the scan length with the axis of rotation of the dosimeter. The scanned area of each slice must be restricted to 90% of the diameter of the dosimeter. Errors in beam wandering across the face of the detector need to be compensated by the addition of a diffusing window and a converging lens. The most objectionable feature of this scanner is its long acquisition time. The total data acquisition time for a 60×60 pixel image was six minutes. Imaging of another object required approximately 2 seconds per profile, leading to an imaging time of about 12 minutes per slice. Total acquisition time for dosimeters of clinically relevant volume can exceed eighteen hours. True three-dimensional scans, with isotropic high resolution and a large field-of-view in the slice direction are not feasible using this methodology, particularly on a routine clinical basis. The plastic PRESAGE dosimeters have been successfully scanned with this type of laser scanner geometry (Sakhalkar et al, *Medical Physics* 2009, 71-82).

A second scanner geometry and the first scanner demonstrating the utilization of a liquid RI matching media is based on cone-beam geometry developed by Appleby (Fried, R. Optical Imaging of Radiation Dose Distributions in a Ferrous-Gelatin-Xylenol Orange Gel Dosimeter, PhD Dissertation, Rutgers, May 1995 and R. Wolodzko, J. et al, 1999, *Medical Physics*, 26(11) 2508-2513). This apparatus utilizes a LED light source with a CCD based area detector and a lens arrangement to deliver parallel beams through a dosimeter immersed in RI matching liquid. As with the gelatin based dosimeter, the dosimetric matrix must be enclosed in a container. The same scanner was disclosed in CA Pat No. 2,495,304 in which the dosimeter was prepared in glass vial containing a diacetylene radiochromic dye, a polymeric binder, solvent and an activator. After irradiation the sample was heated at 60° C. in an oven for 30 minutes. The color disappears after 8 hours. The dosimeter was manually rotated over 360° of rotation using 31 equally spaced acquisition angles. A second optical system also based on cone-beam geometry (Jordan, J. et al, 2001 DOSGEL 2001, $2^{nd}$ International Conference on Radiotherapy Gel Dosimetry, Brisbane, 2001) has been commercialized (Vista™, Modus Medical Devices, Inc., London, ON). The plastic PRESAGE dosimeters have been successfully scanned with this type of scanner geometry (Alqathami, *International Journal of Radiation Oncology* 2012 IC3DDose 2012, 84, e549-e555.)

A third optical CT scanner design also utilized a CCD area detector and a LED light source with a lens arrangement to deliver parallel beams through a dosimeter immersed in RI matching liquid. (Bero, M. et al, 1999, DOSEGEL, 1999, 1st International Workshop on Radiation Therapy Gel Dosimetry, Kentucky). The data was treated with FBP algorithms and reconstructed into a three-dimensional image. The geometry was refined by Oldham (Thomas, A. et al. 2011 *Medical Physics* 38, 4846-4857) to include matched telecentric source and imaging lens with a ⅔" CCD array. The light source is a 3 W red LED behind a weak optical diffuser and a narrow band pass filter (632 nm). The diffuser helps improve the uniformity of flood field, and de-sensitize the system to Schlieren bands in the dosimeter, while the filter reduces any spectral artifacts. Nominally parallel light projects through an aquarium containing a radiochromic dosimeter (PRESAGE) and index matching fluid to minimize bending and reflections at the dosimeter-fluid interfaces. When the scanning is complete, a three-dimensional image is reconstructed after the data is subjected to filtration and back-projection (FBP) algorithms. A PRESAGE dosimeter shaped as a truncated sphere and within a metallic collimator were used to detect radiation contaminated hot cells (U.S. Pat. No. 8,399,859 to Stanley).

Doran (U.S. Pat. No. 7,633,048) disclosed scanning devices which measure and quantify optical properties within a PRESAGE dosimeter through the use of two rotating plane mirrors and two paraboloid mirrors, a laser light beam was made to traverse the object to be scanned wherein the beam was always parallel to the optical axis. The invention provided an improvement over previously reported scanning devices by virtue of increased speed and resolution. Two-dimensional projections gleaned by each scan of the object were reconstructed into a three-dimensional image through the use of various computer techniques. Although an improvement over previous OCT scanners, this invention shared the disadvantage of requiring RI matching liquid.

Adamovics disclosed in U.S. Pat. No. 7,098,463 an optically transparent plastic dosimeter made of polyurethane, which is discriminated from conventional dosimetric polymer scattering gels, known by the trade name PRESAGE (vide supra). The dosimetric polymer gels are translucent, prepared from aqueous precursors, and must be constrained in a container. The optical plastic is substantially transparent, formed from water-insoluble precursors, and is fabricated into any desired shape without the need for a container in the finished dosimeter. The dosimeter is formulated from water-insoluble pre-polymers and one or more water-insoluble color-forming reporter molecule resulting in a shaped solid substantially transparent optical plastic in which a colored image forms upon irradiation with little or no light scattering. After irradiation, the dosimeter is placed in a non aqueous RI solvent of 1.50 for OCT, the dosimeter is rotated repeating the steps of illumination the dosimeter with a light source, detecting light from the dosimeter and processing the detected light to construct a 3D image. Virtually all the dosimeter volume is scanned.

There is a need for refractive index-matching media which is durable, easily utilized, and free from the aforementioned disadvantages. In an early approach, a scanner was disclosed which contains no liquid refractive index matching solvent but utilizes the cylindrical geometry of a container to obtain the desired paths of the scanning light rays through the imaged object originating from a laser source (Maryanski, M and Renade, M., *Proceedings of SPIE* Volume 4320 *Medical Imaging* 2001: Physics of Medical Imaging, Larry E. Antonuk, Martin J. Yaffe, Editors, June 2001, pp. 764-774). This system is intended for use with polymer gel dosimeters constrained in a transparent container, such as a glass jar, and relies upon the detection of polymerized regions within the gel through scattering of incident light. This so-called "dry scanner" suffers from several disadvantages. Foremost, only one-ninth (11%) of the volume of the polymer gel dosimeter is available for scanning. This is due to the fact that unacceptable refractions and aberrations occur when scanning is attempted in regions beyond one-third (33%) of the radius of the device. Thus, a cylindrical jar containing polymeric gel of radius r contains a useful volume of only r/3. As the volume of a cylinder varies as the square of the radius, then eight-ninths (89%) of the polymeric gel within the device is superfluous. This drawback dramatically increases the cost and disposal concerns of using such a system.

Wuu et al (Medical Physics, 2003. 30 (2) 132-137) disclosed a OCT scanner which did not employ RI matching fluid, however ⅔ of the dosimeter is not scanned due to refraction. In a similar approach Papadakis et al (*Medical Imaging, IEEE Transactions*, 2010, 29 (5) 1204-1212) disclosed a large volume of the dosimeter is not adequate for quantitative dosimetry. Doran (US Pat Appl 2012/0170049 and *Phy Med Biol*, 2012, 57 665-683) also without using a RI matching liquid describes the bending of light rays using a reconstruction method known as Algebraic Reconstruction Technique (ART) as does Oldham (Rankine et al *Medical Physics*, 2013, 40 051701-1-051701-8). The conclusion is that even though ART is feasible, these approaches do not adequately solve the problem, as they are ineffective near the periphery of the dosimeter.

Another 3D dosimeter approach that does not employ RI matching fluid was described by Moscovitch et al (U.S. Pat. No. 5,498,876). The invention describes a solid acrylic polymer dosimeter, which contains a light-sensitive dopant molecule, dispersed throughout the medium. The dosimeter is pre-activated by simultaneously exposing parts of the dosimeter to two laser beams at right angles to each other, which traverse the volume of the dosimeter. The dopant molecule interacts simultaneously with two photons, and is thereby transformed to an unstable, higher-energy state. Upon irradiation with high-energy radiation such as neutron beam, the high-energy molecule is induced to revert back to its low-energy form. This reversion is accompanied by fluorescence, which is detected. Designed to be useful as a neutron dosimeter, this device suffers from the limitations of room-temperature instability of the high-energy state of the activated dosimeter, and from the necessity to pre-activate the dopant molecules. The fluorescent read out does not render a full 3D volume but a dot matrix response. Additionally, the volume and dose sensitivity limitations of such a device are described (Moscovitch et al, *Radiation Protection Dosimetry* 2002, 101, 17-22.) In this work, film dosimeters in the range of being 100 um thick to about a centimeter which are not practically useful as 3D dosimeters as practiced in radiation therapy. The dosimeter described by Moscovitch are also have relatively low dose sensitivities of $10^3$-$10^7$ Gy in contrast to the other 3D dosimeters described in the Field of the Invention which have clinically relevant dose sensitivities of at least 1 Gy and above.

BRIEF SUMMARY OF THE INVENTION

The present invention discloses a device to measure optical properties of a three-dimensional transparent dosimeter, and a method to use the device to produce a valid, reproducible, and quantitative image of optical properties across essentially the entire volume of the transparent dosimeter. The invention provides significant and useful improvements over existing practice. The invention provides a scanning instrument, which eliminates the current practice of employing liquid refractive index matching solutions. This is accomplished by using a refractive matching solid containing a dosimeter cavity wherein the transparent dosimeter is inserted.

DETAILED DESCRIPTION OF THE INVENTION

Figure 1:
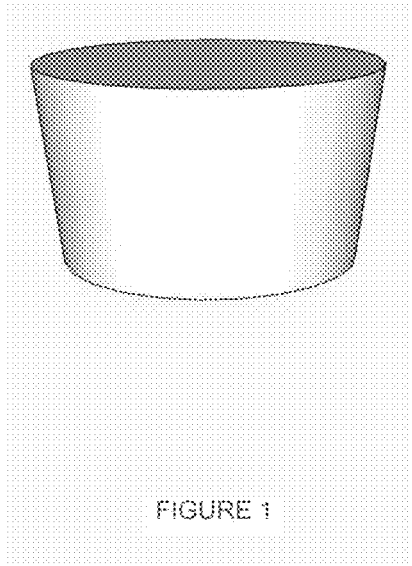
FIG. 1 depicts one non-limiting dosimeter shape of the invention. This inverted truncated cone dosimeter is placed within the cavity of the RI-matching block of the invention for evaluation.
Figure 2:
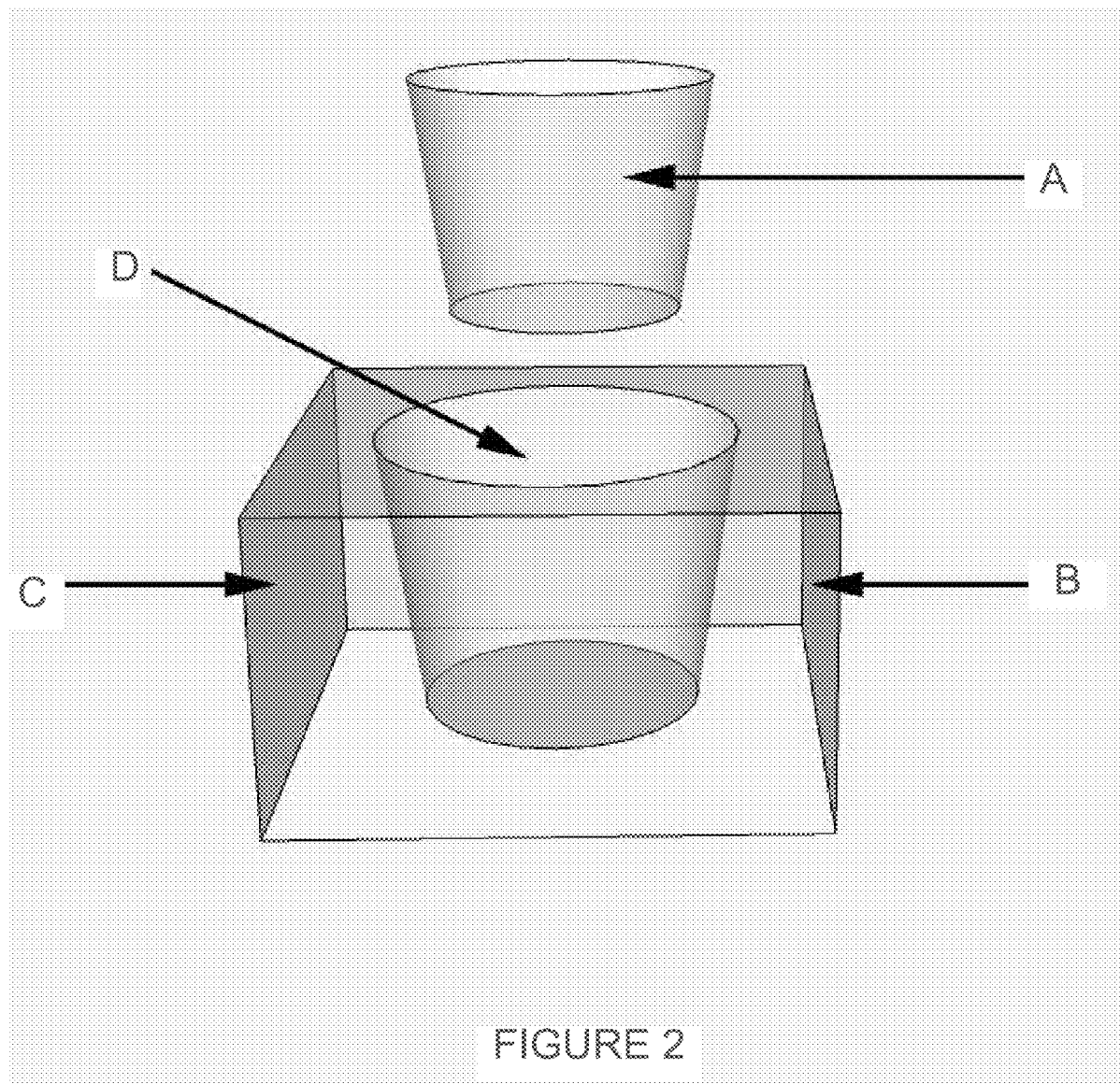
FIG. 2 depicts a non-limiting embodiment of the invention with a shaped dosimeter and an RI-matching block fabricated with a cavity into which the dosimeter is placed for evaluation. A, an inverted truncated cone dosimeter; B, a first face of a transparent RI-matching block; C, a third face of said RI-matching block, wherein B and C are essentially parallel; D, the cavity of said matching block fabricated to accept dosimeter A.
Figure 3:
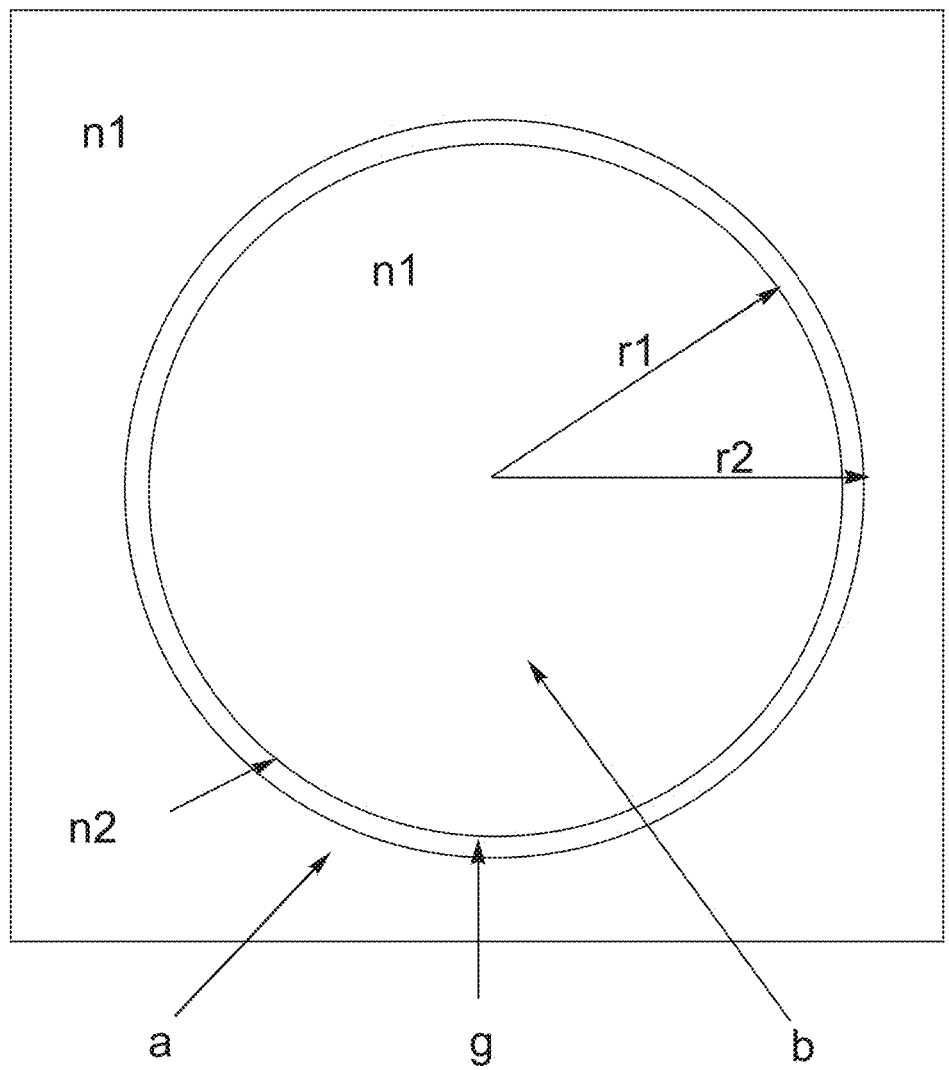
FIG. 3 is a schematic of the view from the top of an assembled dosimeter and RI-matching block. a, RI-matching block; b, dosimeter; g, the interspace between dosimeter and matching block; n1, a first refractive index of the dosimeter and the matching block; n2, a second refractive index of the interspace g; r1, the radius of the top face of the dosimeter; r2, the radius of the top of the matching block cavity.

The present invention is directed to the field of Optical Computed Tomography (CT) dosimetry. Dosimetric devices, or dosimeters, are objects which, after the absorption of radiation, change in a predictable, measurable and quantifiable way as a direct result of the dose of radiation which had been absorbed by the object. In Optical CT dosimetry, liquid, gel, and solid translucent polymeric dosimeters have been fabricated to contain one or more reporter molecules, which have been designed to predictably change one or more physicochemical parameter possessed by the reporter molecule upon absorption of radiation. This is akin to the classical photographic process wherein the interaction of silver halide embedded or attached to the surface of a film undergoes a chemical and physical change upon absorption of visible light. In Optical CT dosimetry, the optimal dosimeter is a transparent three-dimensional object within which is uniformly distributed a reporter molecule which possesses an optical property which predictably changes upon the absorption of radiation. A non-limiting example of such a dosimeter was disclosed (US Pub. Pat. Appn. 2007/0020793 to Adamovics) wherein a transparent cylindrical polyurethane dosimeter, within which was uniformly distributed a colorless leucodye, efficiently mapped the absorption of an applied radiation field due to the transformation of the leucodye to colored species in irradiated domains. The invention disclosed a device, which makes noninvasive, quantitative, and precise measurements of optical properties across the three-dimensional volume of objects, which transmit light. The invention was directed to devices which measure and quantify optical properties which include, but are not limited to, absorption of visible light, absorption of ultraviolet light, absorption of infrared light, refractive index, light scattering, and combinations of these. The invention is used to quantify the three-dimensional distribution of a radiation dose absorbed by an object in which optical properties of the object have been made to change predictably with the interaction with ionizing radiation. In one embodiment, the invention allows the planning and execution of a radiotherapy treatment to be simulated, measured, and evaluated on an inanimate object before applying it to humans and is particularly important for validating complex radiotherapy treatment plans. Without such an experimental measurement, it is impossible to be sure that the dose received by a patient is that predicted by the treatment planning software. The invention provided information by measuring the optical attenuation coefficient (also commonly referred to as optical density) of the sample at all points in the three-dimensional volume. The object is specially designed so that its optical properties (in particular, its absorption or scattering coefficients at the wavelength of operation of the system) change with the absorption of radiation in a predictable and quantitative manner.

The present invention is directed to the improvement of existing technology for measuring ionizing radiation fields. Such radiation fields are in common use in medical radiology, medical radiotherapy, manufacturing and energy production. The monitoring of radiation levels is critical for planned or inadvertent exposure of all life forms to gamma rays, X-rays, cosmic rays, proton, carbon and other ion beams, and other forms of ionizing radiation. In general, embodiments of the invention are useful in the measurement of inadvertent exposure (a non-limiting example is dosimetry badges employed by medical researchers and diagnosticians), measurement of radiation levels in areas with high probability of radiation contamination (non-limiting examples are dosimetry at nuclear facilities for calibration, quality control, and decommissioning purposes and dosimetry mandated by military or Homeland Security officials), and measurements of radiation fields for the planned therapeutic radiation of patients as part of a treatment regimen. In one embodiment of the present invention, noninvasive, quantitative, three-dimensional measurements of the radiation dose absorbed by a dosimetric object are made. The measurement process is comprised of subjecting the dosimetric object to a field or fields of radiation; removing the object from the fields of radiation; placing the object in the scanner of the present invention; scanning the object with light rays and detecting the spatial and intensity aspects of the transmitted light in a three-dimensional array by methods disclosed herein; calculating a three-dimensional image by methods disclosed herein whereby the image represents a true, accurate, and quantitative depiction of the original radiation fields. This allows the process of radiotherapy treatment to be simulated on an inanimate object before applying it to humans and is particularly important for validating complex radiotherapy treatment plans. This planning method is invaluable to caregivers who must plan with as little error as possible the intensity and distribution of therapeutic doses of radiation. It is critical in radiotherapeutic treatment to deliver the appropriate dose to diseased tissues while avoiding irradiation of healthy tissue nearby. In addition, without such an experimental measurement, it is impossible to be sure that the dose received by a patient is that predicted by treatment planning techniques, and is appropriate for chronic or long term radiotherapy treatment.

In one embodiment, the scanner of the present invention, and the method of image reconstruction of the invention, are used with cylindrical previously irradiated three-dimensional dosimeters. The dosimeter, or three-dimensional object, is designed so that its optical properties (in particular, its absorption or scattering coefficients at the wavelength of operation of the system) change with the absorption of radiation in a predictable and quantitative manner. The purpose of the scanner is to measure these optical properties non-invasively at all points in a specified 3-D volume and thus to deduce the dose which had been absorbed by the object.

It is an object of the invention to provide a scanning device which facilitates the transmission of light through a transparent three-dimensional object, the optical properties of said object having been previously altered by interaction with radiation, and said transmission captured by one or more optical detectors, wherein said capture is in the form of digital data stored on computer media, wherein said data is converted by means of the invention to a valid, reproducible, and quantitative three-dimensional image truly representing the said altered optical properties, wherein said transmission and said image encompass the entire volume of said object.

It is another object of the invention to provide a scanner with a solid refractive index medium which facilitates the production of a valid, reproducible, and quantitative image through scanning of the entire volume of a three-dimensional dosimeter for the purposes of planning, mapping, predicting, or verifying radiotherapy for medical treatment purposes, wherein the method of calculation used to produce such an image are substantially those disclosed herein.

It is another object of the invention to provide a scanner with a solid refractive index medium which facilitates the production of a valid, reproducible, and quantitative image through scanning of the entire volume of a three-dimensional dosimeter for the purposes of planning, mapping, predicting, or verifying the irradiation fields in the productive and peaceful use of ionizing radiation, wherein the method of calculation used to produce such an image are substantially those disclosed herein.

In three dimensional dosimetry it is important to create imagable positioning references in or on the dosimeter in order to obtain an accurate 3D radiation map after image reconstruction. These references, also known as fiducial points, are landmarks which allow the correlation between the radiation field and the 3D image acquired by dosimetry and reconstruction. In one non-limiting example, in the evaluation of a clinical radiation treatment plan, the fiducial marker of an irradiated 3D dosimeter is positioned in the optical scanning system so that, after reconstruction, the 3D dosimetric data can be overlapped with the reference marker of the radiation treatment plan. This allows the medical practitioner to verify that an applied radiation field corresponds to the planned therapy.

In one embodiment of the present invention, reference markers can be introduced during the manufacture of the dosimeter. In another embodiment, reference markers may be applied to a fabricated dosimeter. A non-limiting example of incorporating reference markers during the fabrication of a solid shaped plastic 3D dosimeter shaped protrusions are designed to extend from the bottom face.

Reference marker nubs can be cast into the bottom of the dosimeter while the rotation stage of the optical scanning system has the corresponding female coupling piece, corresponding to the protruding nubs of the dosimeter that is referenced to the scanner rotation. Conversely when rotating the 3D dosimeter from above a dove tail reference marker with a slot would be gripped by a dovetail grip attached to the rotary stage of the dovetail grip containing a post.

It will be appreciated by those with skill in the art that the light source, detector, computing equipment, and computer application may be selected from a wide variety of available products. While it was determined that an LED array source provided superior results in the present invention, other light sources may be used and are within the scope of the invention.

While it was discovered that high resolution CMOS and CCD detection systems gave the best results, other light detection equipment might be utilized, and is within the scope of the invention. It was found after much experimentation and testing that a lens partnered with a CMOS detector gave best data when the camera field of view was limited to 15"×15". However, other dimensions may be viable and are within the scope of the invention.

It will be appreciated that several compositions of transparent solid polymeric matrices may be utilized to fabricate solid RI matching blocks and dosimeters. While the exemplary formulations described herein have been found to yield excellent results, other polymeric fabrications might be used, and these are within the scope of the invention.

In the present invention, the purpose of the block is to allow the transmission of light through the block-dosimeter assembly in parallel lines without distortion, refraction, or scattering. For this reason the face of the solid block illuminated by the incident light from the source must be orthogonal to the light path, and the face of the block where transmitted light leaves the block-dosimeter assembly and enters the detector must be orthogonal to the detector, and these faces must be parallel to each other. The distance between these faces and the edge of the dosimeter cavity is designed such that the block may be fabricated, manipulated, and used according to the invention. The faces receiving incident light and transmitting light must be smooth and free of defect. In addition, the dosimeter cavity must be smooth and free of defect. For accurate scanning results, the axis of the dosimeter cavity must be parallel to both of the faces receiving incident light and transmitting light. The cavity is engineered such that the interspace between the edge of the dosimeter and the edge of the cavity is minimized. The range of the interspace is between 0.5 mm and 5 mm.

It will be appreciated that the rotation of a shaped solid dosimeter within the cavity of a RI matching block of the invention wherein the interspace between dosimeter and cavity is very small may be attended by friction. In some embodiments of the present invention, wetting agents, or lubricants may be utilized to reduce such friction and facilitate smooth rotation. In such embodiments, the dosimeter is not immersed into a liquid but is fitted into a corresponding cavity and a minimal amount of wetting agent or lubricant may be sparingly applied. In some embodiments, the employment of wetting agents or lubricants provide the additional advantage of dispelling air from the interspace. The agents or lubricants are selected from those substances which are non-toxic, inexpensive, readily available, free of offensive odor, environmentally friendly, and are readily and safely disposed of. Such substances include, but are not limited to, water, vegetable oils, castor oil, clove oil, lemon oil, orange oil, safflower oil, sunflower oil, oil of wintergreen, mineral oils, paraffin oil, glycerin, glycerol, and immersion oil. It will be appreciated that there are other liquids which may be utilized to fulfill this function, and these are within the scope of the invention.

In one non-limiting embodiment of the invention, a matching block was fabricated as in Example 6 and an irradiated dosimeter as disclosed in U.S. Pat. No. 7,098,463 to Adamovics was fitted. A LED array light source (LightPad, Artograph, Delano, Minn.) was used as the illumination source and a 15"×15" telecentric lens (Light Works, Toledo, Ohio) before an ac2000 CMOS camera (Bassler AG, Ahrensburg, Germany) were utilized.

DEFINITIONS

Figure 4:
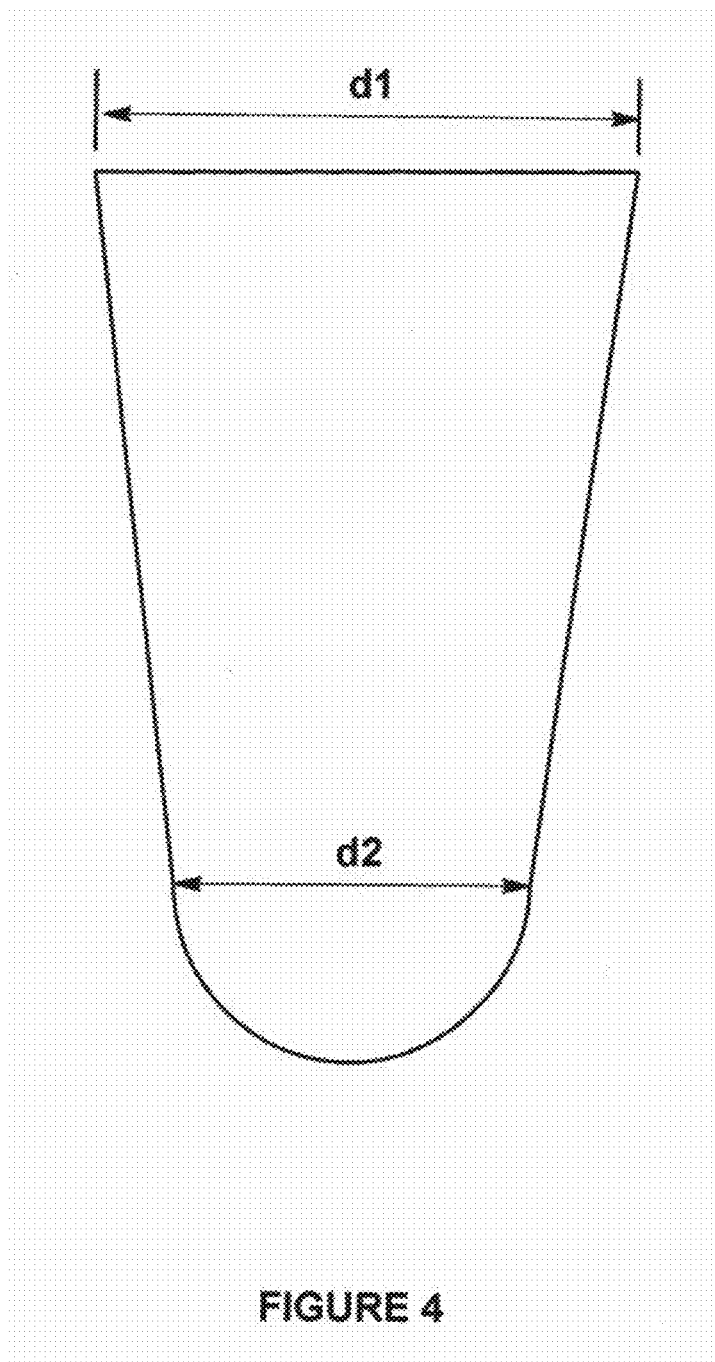
FIG. 4 depicts one non-limiting dosimeter shape of the invention. This inverted truncated cone dosimeter with one convex surface is placed within the cavity of the RI-matching block of the invention for evaluation.
Figure 5:
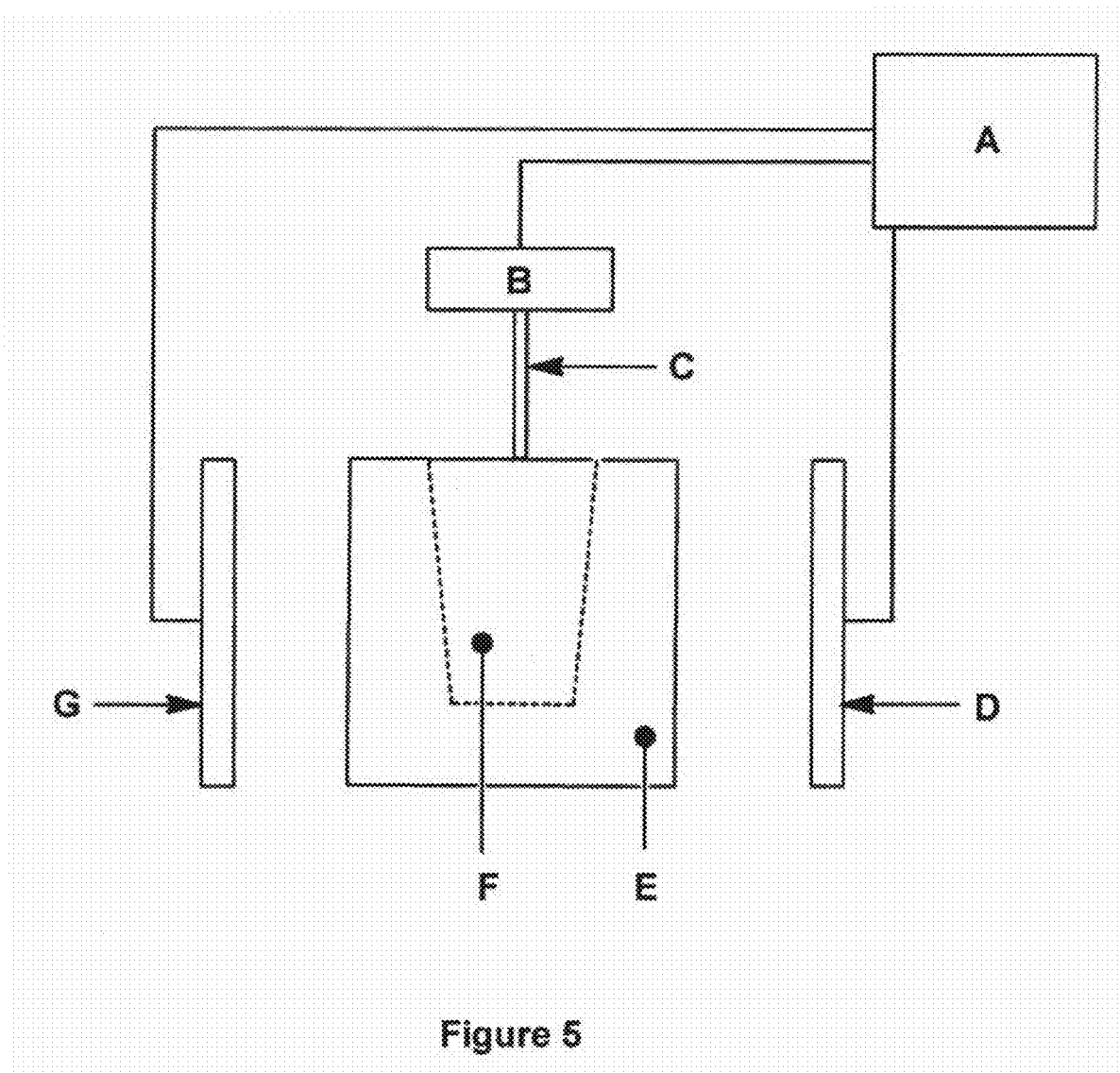
FIG. 5 illustrates the configuration of one embodiment of the invention which incorporates a means to rotate the dosimeter of the invention through a series of stepped angle increments through a connection to a rotation stage (a stepper motor assembly mounted above the RI matching block). A, computer; B, stepper motor; C, rotator shaft; D, light source; E, RI Matching block; F, dosimeter fitted to the cavity of the matching block; G, detector.
Figure 6:
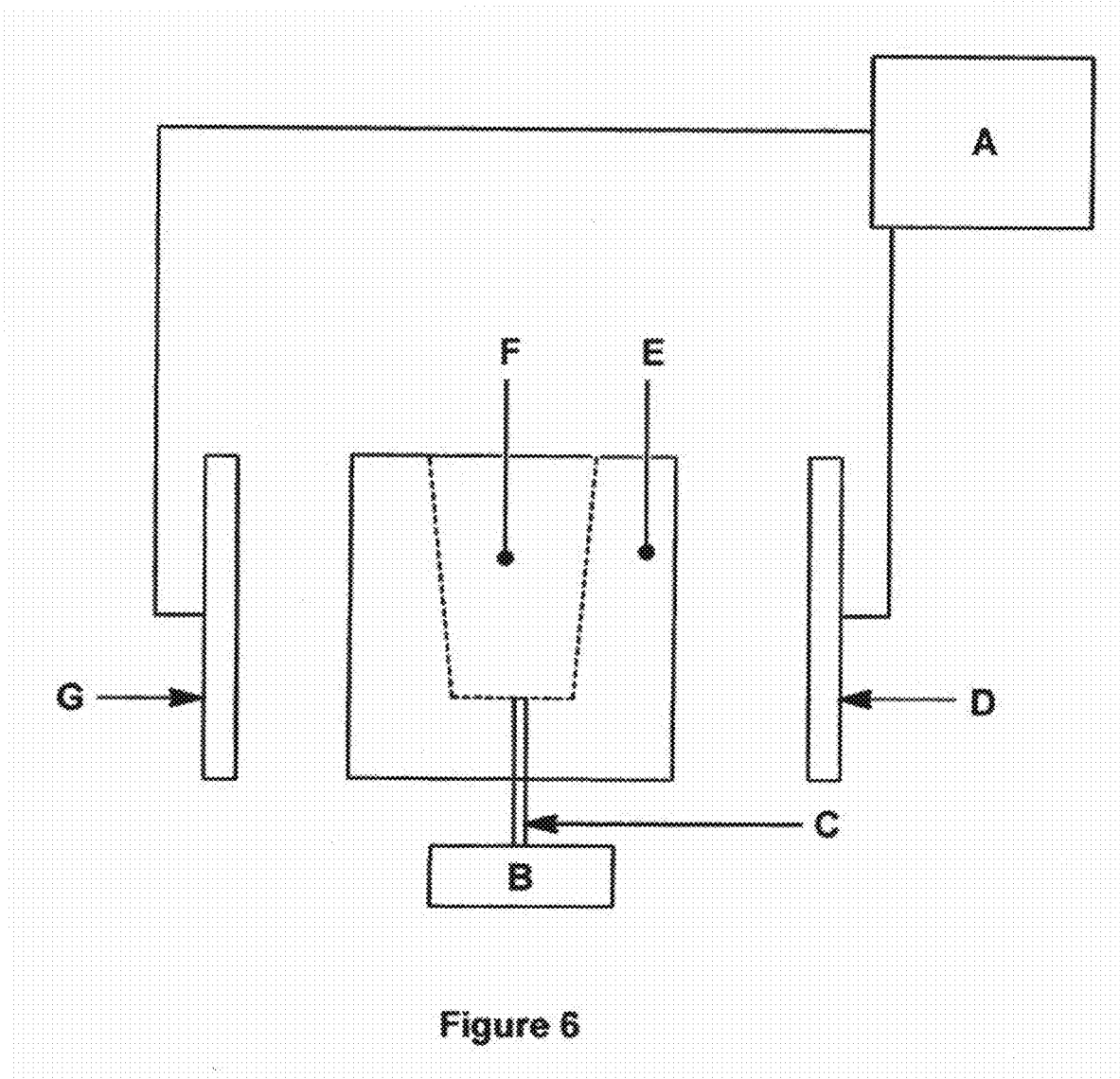
FIG. 6 illustrates the configuration of one embodiment of the invention which incorporates a means to rotate the dosimeter of the invention through a series of stepped angle increments through a connection to a rotation stage (a stepper motor assembly mounted below the RI matching block.) A, computer; B, stepper motor; C, rotator shaft; D, light source; E, RI Matching block; F, dosimeter fitted to the cavity of the matching block; G, detector.

PRESAGE: the solid transparent dosimeter disclosed in US Patent transparent: transmitting light with no obfuscation, clear, free of cloudiness block: solid piece, to be discriminated from "tank" or "film". A block shall not be considered a tank with wide or thick walls dosimeter cavity: fabricated recess, vacuity, hole, chamber, pocket within the solid transparent block of the invention inverted truncated cone: having essentially the shape of a cone of radius r1 which is truncated by a plane essentially parallel to the cone face containing r1 to give a second face having radius r2; wherein r1>r2; a solid having essentially the shape portrayed in FIG. 1.

inverted truncated cone with one convex face: having essentially the shape of a cone with diameter d1 which is truncated at a second diameter d2, wherein d1 is greater than d2 and the surface of the solid at d2 is made to be essentially convex, or caused to be in the shape of the exterior of a sphere, a solid having essentially the shape portrayed in FIG. 4.

interspace: the gap or void between the transparent block and the dosimeter of the invention when the dosimeter is fitted into the dosimeter cavity. It is one object of the invention to minimize the interspace air: room atmosphere in the interspace which is not displaced when the dosimeter is fitted into the dosimeter cavity data from detector: electronic signal representative of the differences in light absorption in an irradiated dosimeter of the invention rotary stage: a motorized mechanism to cause rotation of a dosimeter within the cavity of a RI matching block of the invention wherein rotation is made to proceed in either clockwise or counterclockwise fashion in a plane essentially perpendicular to the axis of the dosimeter, and wherein said rotation proceeds while maintaining an essentially parallel alignment of the axis of the dosimeter and the axis of the cavity of the block reconstruction: computerized tomographic process whereby single slices measured by the scanner of the invention are assembled into a three-dimensional image which may be displayed on a computer monitor or other viewing device information contained within dosimeter: differences in optical properties caused by interaction of reporter molecules within the dosimeter and an applied field of radiation fiducial points: reference markings appearing on the dosimeter of the invention and on the mechanism to perform rotation of the dosimeter within the dosimeter cavity. These fixed points or lines allow indexing to the rotary stage starting at 0 degrees lubricant: a substance to reduce the friction between dosimeter and cavity.

EXAMPLES

Materials used were obtained from the following manufacturers: Crystal Clear 206 Part A 200, Part B clear liquid plastic polyurethane from Smooth-On., Easton, Pa.: Poly-Optic 14-70 Part A, Poly-Optic 14-70B polyurethane, Platsil 75-25 parts A & B platinum silicone mold rubber, Universal Release liquid and GlassRub from PolyTech Development Corp., Easton, Pa. Clear plastic sheets were obtained from McMaster Carr, Robbinsville, N.J. Acrylic plastic risers (¼") were obtained from Tap Plastics. Rotary stage was obtained from Velmex Inc. Light Works, LLC built the Telecentric lens.

Example 1

The RI solid media was made by using an acrylic box which was assembled using four 6"×6" acrylic sheets (0.5" thick) with a base 6"×5¼" with a centered 1" hole. To create an area below for what will be the optical scanner systems turntable for rotating the dosimeter at the bottom of the assembled box centered over the hole a cylinder of ¾" ht×4½" diameter Platsil mold rubber was placed. Crystal Clear 206 liquid polyurethane containing 5% butyl acetate, 2% DMSO and 0.4% carbon tetrabromomethane dissolved in 0.2% tetrahydrofuran was poured around the Platsil rubber and the box was pressurized at about 50 psi for 48 hours. After the polyurethane hardened the Platsil rubber positive was removed. Placed above the cavity created after removal of the Platsil rubber an approximate 1 Kg PTFE cylinder with diameter of 12 cm and 13 cm in height was placed. Approximately 2 Kg of Crystal Clear 206 liquid polyurethane was poured around the PTFE positive. After the polyurethane cured under 50 psi pressure for 48 hours it was removed to create a cavity in which the 1 Kg PRESAGE dosimeter fits.

Example 2

A plastic box with a dosimeter cavity was created using Platsil mold rubber. Inside a 12 L polypropylene container was poured a 300 g base of Platsil liquid rubber, which hardened within 24 hours. To an acrylic box as described in Example 1 (without the added polyurethane) four scratch resistant acrylic sheets (6"×6", ¼" thick) were taped to the four sides of the box. The acrylic box was placed on top of the Platsil rubber base and 5.5 Kg of the Platsil liquid rubber was poured around the box including and inside the hole at the bottom of the acrylic box. After the molding rubber hardened the acrylic box was removed. The four scratch resistant acrylic sheets were placed within the rubber mold impressions created by the acrylic box. About 300 g of polyurethane was poured into the base of the mold after around the ¾" ht×4½" diameter Platsil rubber mold. This was followed by the addition of the 1 Kg PTFE cylinder. 2 Kg of Crystal Clear 206 containing 5% butyl acetate, 2% DMSO and 0.4% carbon tetrabromomethane dissolved in 0.2% tetrahydrofuran were poured into the Platsil rubber mold and pressurized at about 50 psi for 48 hours. After the polyurethane hardened the Plasil rubber positive mold and positive were removed to create a cavity in which the 1 Kg PRESAGE dosimeter fits and 4 sides of the dosimeter with scratch resistant acrylic sides.

Example 3

A box was made by gluing two scratch resistant ¼"×6"×6" polycarbonate sheet to the two ends of an acrylic ¾"×6"×6" riser. A 1" hole was drilled into the base of the box. About 200 g of polyurethane was poured into the base of the box around the ¾" ht×4½" diameter Platsil rubber mold. After hardening the 1 Kg PTFE cylinder positive was added and 1.5 Kg of polyurethane containing 5% butyl acetate, 2% DMSO and 0.4% carbon tetrabromomethane dissolved in 0.2% tetrahydrofuran poured around the PTFE and pressurized at about 50 psi for 48 hours. After the polyurethane hardened the Plasil rubber positive mold and PTFE positive were removed to create a cavity in which the 1 Kg PRESAGE dosimeter fits and 2 sides of the dosimeter are scratch resistant polycarbonate sides.

Example 4

An acrylic box 6×6×6 inch with sides 0.25 inch thick was purchased from Choice Acrylic Displays (New Mexico). The 1 Kg PTFE cylinder positive was centered at the base of the box and 1.5 Kg of polyurethane containing 5% butyl acetate, 2% DMSO and 0.4% carbon tetrabromomethane dissolved in 0.2% tetrahydrofuran poured around the PTFE and pressurized at about 50 psi for 48 hours. After the polyurethane hardened the Plasil rubber positive mold and PTFE positive were removed to create a cavity in which the 1 Kg PRESAGE dosimeter fits.

Example 5

The RI solid media was made by using an acrylic box which was assembled using four 6"×6" acrylic sheets (0.5" thick) with a base 6"×5¼" with a centered 1" hole. The sheets were screwed together. The 1 Kg PTFE cylinder positive was centered at the base of the box and about 1.5 Kg of polyurethane containing 5% butyl acetate, 2% DMSO and 0.4% carbon tetrabromomethane dissolved in 0.2% tetrahydrofuran poured around the PTFE and pressurized at about 50 psi for 48 hours. After the polyurethane hardened the PTFE positive was removed and the acrylic box was disassembled. The turntable for rotating the dosimeter was attached to the bottom of the RI media cavity.

Example 6

The box used to make the RI solid media was assembled using four 6"×6" polycarbonate sheets (0.5" thick) with a base 6"×5¼" that were glued together using Poly GlassRub50. The 1 Kg aluminum cylinder positive was centered at the base of the box and about 1.5 Kg of polyurethane containing 5% ethyl acetate, 2% DMSO and 0.5% carbon tetrabromomethane dissolved in 0.2% tetrahydrofuran poured around the PTFE and pressurized at about 50 psi for 48 hours. After the polyurethane hardened the aluminum positive was removed and the acrylic box was disassembled. The turntable and a stepper motor for rotating the dosimeter were attached to the bottom of the RI media cavity which was set in front of a TLCF-035 Fresnel telecentric lens and a Basler ac2000 CMOS camera.

I claim:

1. An assembly for refractive index matching in Optical Computerized Tomography scanning comprising:
    a light source,
    a light detector,
    a transparent solid plastic block fabricated with a dosimeter cavity, wherein the shape of the said dosimeter cavity is selected from the set consisting of essentially a cylinder, essentially an inverted truncated cone, essentially an inverted cone with one convex face, and essentially identical to the dosimeter;
    an irradiated dosimeter inserted into said cavity; so that the interspace between the edge of said cavity and the edge of said dosimeter is between 0.5 and 5 mm;
    a mechanism to cause the rotation of the dosimeter within the dosimeter cavity; and
    a computer programmed to store data from said detector, and perform the reconstruction of said data to render a three-dimensional image representing the information contained within said irradiated dosimeter.

2. The assembly of claim 1 wherein the said block has a first face, a second face, a third face, a fourth face, a fifth face, and a sixth face; and
    wherein said first face and said third face are essentially parallel; wherein the axis of said cavity is essentially parallel to said first face and is essentially parallel to said third face; and
    wherein the axis of said dosimeter is essentially parallel to said first face and is essentially parallel to said third face; and
    wherein the distance from the edge of the dosimeter cavity to said first face is in the range of 1 mm to 25 mm; and
    wherein the distance from the edge of the dosimeter cavity to said third face is in the range of 1 mm to 25 mm; and
    wherein said mechanism is a rotary stage
    wherein the said interspace is in the range of 0.5 mm to 5 mm.

3. An optical scanning method comprising the steps of:
    a) inserting an irradiated dosimeter into a transparent solid plastic block fabricated with a dosimeter cavity, wherein the shape of the said dosimeter cavity is selected from the set consisting of essentially a cylinder, essentially an inverted truncated cone, essentially an inverted cone with one convex face, and essentially identical to the dosimeter;
    b) causing the transmission from a light source to pass through said block and said dosimeter;
    c) causing the optical data produced by said transmission to be captured by a detector;
    d) storing said data in a computer;
    e) causing the rotation of said dosimeter within said cavity;
    f) repeating steps b, c, d, and e a multiplicity of times;
    g) causing a computerized tomographic reconstruction using said stored data.

* * * * *